United States Patent
Mita et al.

(10) Patent No.: US 6,350,605 B1
(45) Date of Patent: Feb. 26, 2002

(54) MICROORGANISMS, MICROBIAL SYMBIONTS, THEIR CULTURE METHODS, AND METHODS FOR TREATING MANGANESE-CONTAINING WATER USING THEM

(75) Inventors: Naoki Mita, 115-202,Namili 2-Chome, Tsukubi-shi, Ibaraki, 305-0044; Yoshishige Kato, 460-23, Kamihirooka, Tsukuba-shi, Ibaraki, 305-0041; Akihiko Maruyama; Takanori Higashihara, both of Tsukuba; Yutaka Kanai, 50-1-16, Hitachino-higashi, Ushiku-shi, Ibaraki, 305-1200; Akira Usui, Tsukuba; Hiroyuki Miura, Sapporo; Takashi Ito, Mito; Hidetoshi Tashiro, Musashino, all of (JP)

(73) Assignees: Naoki Mita; Yoshishige Kato; Yutaka Kanai, all of Ibaraki (JP)

( * ) Notice: Subject to any disclaimer, the term of this patent is extended or adjusted under 35 U.S.C. 154(b) by 0 days.

(21) Appl. No.: 09/470,147

(22) Filed: Dec. 22, 1999

(30) Foreign Application Priority Data

Dec. 28, 1989 (JP) ............................................. 10-377190
Apr. 20, 1999 (JP) ........................................... 11-112735

(51) Int. Cl.$^7$ .................................................. C12N 1/20
(52) U.S. Cl. ................................ 435/252.4; 435/252.1; 435/168; 435/42; 424/93.3
(58) Field of Search .......................... 435/251.1, 252.4, 435/42, 168; 424/93.3

(56) References Cited

PUBLICATIONS

"Mechanism of the Oxidatio of Divalent Iron And Manganese By Iron Developing In A Neutral Acidic Medium", vol. 47(4):591–9, Jul.–Aug. 1978.

"The Potential Use of Manganese Oxidation In Treating Metal Effluents", vol. 9(12):1253–1261, (1996).

"Microalgal–Facilitated Bacterial Oxidation of Maganese", vol. 16(5):267–273, (1996).

"A Growing Deposit of Hydrous Manganese Oxide Produced by Microbial Mediation At A Hot Spring", vol. 28(2):71–80, (1994).

Muneo et al., "Removal Of Manganese With Microbe", Japanese Patent Abstract No. 59–177198, (1983).

Stuetz et al., J. Ind. Microbiol. 1996, 16(5), 267–273.*

Mita, et al., REWAS '99—Global Symp. Recycl., Waste Treat. Clean Technol., Proc. (1999), vol. 3, 2347–2356.*

* cited by examiner

*Primary Examiner*—Irene Marx
(74) *Attorney, Agent, or Firm*—Foley & Lardner

(57) ABSTRACT

This invention relates to a novel microorganism capable of oxidizing manganese such as the genus Cedecea bacterium GSJ/MITA24A/ASHO-RO/1, the genus Aeromonas bacterium GSJ/MITA24B/ASHO-RO/2, or the genus Shewanella bacterium GSJ/MITA24C/ASHO-RO/3; to a method for removing manganese from water containing manganese, which comprises contacting the water containing manganese with a microbial symbiont of algae and one or more microorganisms capable of oxidizing manganese to oxidize and precipitate the manganese, thereby removing the manganese from the water; and to a method of recycling the recovered manganese.

7 Claims, 2 Drawing Sheets

MICROORGANISMS, MICROBIAL SYMBIONTS, THEIR CULTURE METHODS, AND METHODS FOR TREATING MANGANESE-CONTAINING WATER USING THEM

FIELD OF THE INVENTION

The present invention relates to a novel microorganism capable of oxidizing manganese; to a microbial symbiont of algae and one or more microorganisms chosen from the genus Cedecea bacterium GSJ/MITA24A/ASHO-RO/1, the genus Aeromonas bacterium GSJ/MITA24B/ASHO-RO/2, and the genus Shewanella bacterium GSJ/MITA24C/ASHO-RO/3; to a method for culturing the microbial symbiont in a solution of artificial seawater (Kester) diluted with water; to a method for removing manganese from water containing manganese using the symbiont; and to a method for using the recovered manganese.

BACKGROUND OF THE INVENTION

Various methods for removing heavy metals, particularly manganese, from water containing them are known. Among them, a chemical treatment for the removal of manganese comprises adjusting water containing manganese ions to a strong alkalinity of pH 10 or more to precipitate manganese dioxide, separating and removing the resulting manganese dioxide from the water, then neutralizing and discharging the manganese-free water. A microbial method for the removal of manganese requires the addition of a large amount of organic matter as nutrients. In addition, it often utilizes only microorganisms capable of removing manganese, obtained through their separation and purification, and so the microorganisms may lose their ability to remove manganese during the subculture and storage of them. Any of these methods cannot satisfy demands on costs and removal performance. Therefore, development of low-cost and effective methods for removing manganese from water has been expected.

Under these circumstances, objects of the present invention are to find the existence of a novel microorganism and a microbial symbiont thereof both having an ability to efficiently remove heavy metals, particularly manganese, and to provide the novel microorganism, the microbial symbiont, a method for culturing the microbial symbiont, a method for removing manganese from water containing manganese, and a method for recycling manganese recovered.

SUMMARY OF THE INVENTION

The present inventors have achieved the present invention by finding the fact that in water a particular microbial symbiont has an ability to capture heavy metals, particularly solid manganese, and an ability to oxidize dissolved manganese so as to precipitate it. The present invention is as follows.

(1) A microbial symbiont of manganese oxidizing bacterium and algae.

(2) A microbial symbiont as described in (1), said algae comprises one or more algae chosen from blue-green algae (cyanobacteria) such as Oscillatoria; diatoms such as Navicula; and green algae such as Ulothrix.

(3) A microbial symbiont as described in (1) or (2), said manganese oxidizing bacterium comprises one or more bacteria chosen from the genus Cedecea bacterium GSJ/MITA24A/ASHO-RO/1, the genus Aeromonas bacterium GSJ/MITA24B/ASHO-RO/2, and the genus Shewanella bacterium GSJ/MITA24C/ASHO-RO/3.

(4) The genus Cedecea bacterium GSJ/MITA24A/ASHO-RO/1 capable of oxidizing manganese.

(5) The genus Shewanella bacterium GSJ/MITA24C/ASHO-RO/3 capable of oxidizing manganese.

(6) A method for culturing a manganese oxidizing bacterium, wherein the culture is conducted in a solution of artificial seawater (Kester) diluted with water supplemented with organic nutrients.

(7) A method for culturing microbial symbiont as described in (1) or (2), wherein the method comprises culturing the symbiont in a solution of artificial seawater (Kester) diluted with water in the presence of a sludge of manganese mineral deposit and in the absence of organic matter.

(8) A method as described in (6) or (7), wherein 0.5- to 20-fold dilution of artificial seawater (Rester) is used.

(9) A method, as described in (8), wherein the microorganism is grown at a pH of 5 to 8 only with sunlight.

(10) A method for treating water containing manganese, wherein the method comprises contacting the water containing manganese with a manganese oxidizing bacterium to oxidize and precipitate the manganese, thereby removing the manganese from the water.

(11) A method for treating water containing manganese, wherein the method comprises contacting the water containing manganese with a microbial symbiont of manganese oxidizing bacterium and algae to oxidize and precipitate the manganese, thereby removing the manganese from the water.

(12) A method as described in (10) or (11), wherein said manganese oxidizing bacterium comprises one or more bacteria chosen from the genus Cedecea bacterium GSJ/MIT24A/ASHO-RO/1, the genus Aeromonas bacterium GSJ/MITA24B/ASHO-RO/2, the genus Shewanella bacterium GSJ/MITA24C/ASHO-RO/3.

(13) A method for recycling the recovered manganese as described in (10) or (11), wherein the method comprises recycling the recovered manganese as a material for manufacturing products such as dry cells, glazes, iron, glasses.

DESCRIPTION OF THE PREFERRED EMBODIMENTS

Figure 1:
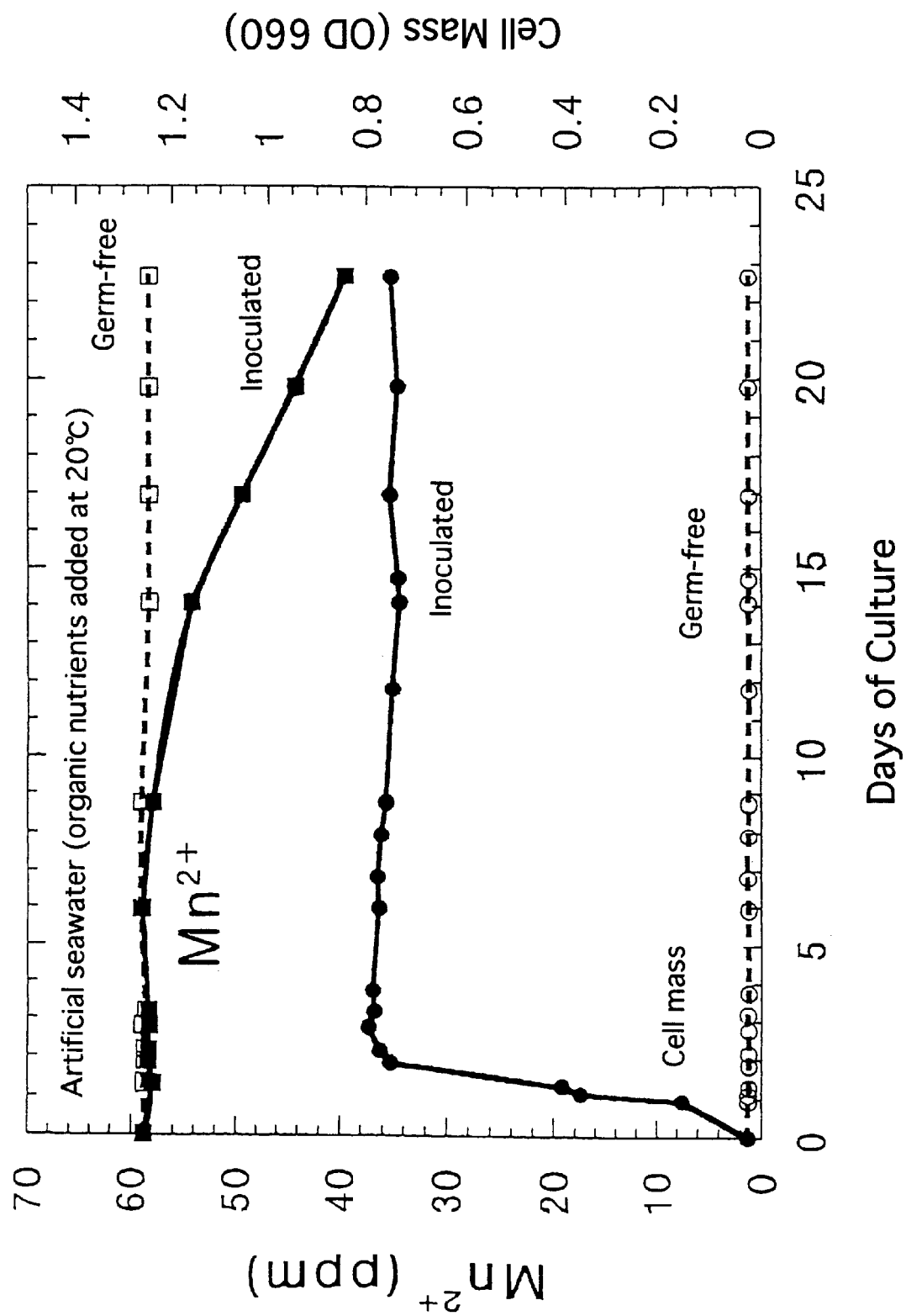
FIG. 1 shows the growth curve of the microorganism of the present invention and its effect of the removal of manganese.

The microbial symbiont of the present invention can be obtained from the natural environment, in particular from manganese precipitates in water that contains manganese ions dissolved therein or from manganese precipitates around such environment. Preferably the microbial symbiont can be obtained from a place with less organic matter under moderate irradiation of light.

The novel manganese oxidizing microorganisms including the genus Cedecea bacterium GSJ/MITA24A/ASHO-RO/1, the genus Aeromonas bacterium GSJ/MITA24B/ASHO-RO/2, and the genus Shewanella bacterium GSJ/MITA24C/ASHO-RO/3, and the symbiont of one or more manganese oxidizing microorganisms above and algae, can be cultured in a large scale. Examples of the above described algae include blue-green algae (Cyanobacteria), such as Ocillatoria; diatoms, such as Navicula; and green-algae, such as Ulothrix. In the above described culture method, it is preferable to conduct the culture in acidic or weakly alkaline water with pH 5 to 8 but without organic matter only with sunlight.

Thus, the cell culture can be obtained by the very simple method that requires no artificial addition of organic matter as nutrients.

The following Examples will be given for illustration of the present invention, but it is intended that the scope of the invention should not be limited to the Examples.

EXAMPLES

Example 1

(1) Source of Microorganisms

Microorganisms of interest were obtained from natural environment.

(2) Sampling of Microorganisms

Bacteria were obtained from samples of a colony of microalgae that includes blue-green algae (cyanobacteria) such as Oscillatona, diatoms such as Navicula, or green algae such as Ulothrix, of precipitate of manganese dioxide, or of the aggregation composed of the two. Typically, 1 ml of a sample obtained from a portion of the algae in between the surface and the 3 mm below the surface, was added to 9 ml of water to provide a total volume of 10 ml.

The obtained microorganism has been found to contain three kinds of microorganisms by the experiments as shown below. However, the deposition of the mixed microorganisms, named GSJ-MITA-ASHORO-MN-MAT-1, was rejected by the depositary authority National Institute of Bioscience and Human Technology, Agency of Industrial Science and Technology (1-3, Higashi 1-chome, Tsukuba-shi, Ibaraki-ken, 305-0046 Japan), because these organisms could not be preserved under freezing.

(3) Growth, Screening, and Isolation of Manganese Oxidizing Bacteria

A 20% solution of artificial seawater (Kester) (KSW:Kester et.al., Limnol. Oceanogr. 12, 176–179, 1967) was prepared as an artificial solution of inorganic salts in water with concentrations of salts similar to the hot-spring composition. Suspension obtained through serial dilution of the above described sample with the artificial solution of inorganic salts in water was applied to an agar plate medium (which was prepared with a modified YF1-Mn medium (Mita et al., Geochem. J. 28, no.2, 71–80, 1994) where the concentration of KSW is 20% in 1/2 TZ-Mn medium (Maruyama et al., J. Oceanogr. 49, 353–367, 1993)), and was cultured and grown at 20° C. or 37° C. Only colonies capable of changing color of an aqueous TMBZ.HCl solution to blue were screened from colonies that have appeared on the medium, colonies having different shapes were separated from each other, then a strain was isolated. For convenience, the names of the strains are as follows: Mn-24 (A) is referred to as GSJ/MITA24A/ASHO-RO/1 strain, Mn-24(B) as GSJ/MITA24B/ASHO-RO/2 strain, and Mn-24(C) as GSJ/MITA24C/ASHO-RO/3 strain.

(4) Identification of Manganese Oxidizing Bacteria

The identification of the strains was consigned to Japan Food Research Laboratories. Morphological observation, tests of physiological properties, and mesurements of type of quinone and of GC content of intracellular DNA for the strains were performed, and thus the strains were identified by referring to Krieg and Holt, "Bergey's Manual of Systematic Bacteriology", Vol.1, 1984, Williams & Wilkins), Holt et al. ("Bergey's Manual of Determinative Bacteriology", Ninth Edition, 1994, Williams & Wilkins), MacDonell and Colwell (System. Appl. Microbiol., 6, 171, 1985), Lee et al. (J. Gen. Microbiol., 98, 439,1977), or Nozue et al. (Int. J. System. Bacteriol., 42, 628, 1992).

(5) The mycological properties of GSJ/MITA24A/ASHO-RO/1 and the identified strain were as follows. This strain was the closest to the genus Cedecea. That is, though it showed no production of lipase, which is a characteristic of the genus Cedecea, it showed character similar to that of *Cedecea davisae* belonging to the family enterobacterium, and was an oxidase-negative facultative anaerobic Gram-negative rod. This novel microorganism was designated as the genus Cedecea bacterium GSJ/MITA24A/ASHO-RO/1, and deposited with National Institute of Bioscience and Human Technology, Agency of Industrial Science and Technology (1-3, Higashi 1-chome, Tsukuba-shi, Ibaraki-ken 305-0046, Japan), as GSJ/MITA24A/ASHO-RO/1. The accession number assigned was FERM P-17064. This deposition was thereafter transferred to an international deposition under the terms of the Budapest Treaty on Dec. 17, 1999, and the accession number FERM BP-6974 was assigned.

Mycological properties of the strain GSJ/MITA24A/ASHO-RO/1:

| (Test Items) | (Test results) |
|---|---|
| Morphological characters | rod |
| Gram stain | − |
| Spores | − |
| Motility | + |
| Flagella | peritrichal |
| Behavior toward oxygen | facultative anaerobic |
| Oxidase | − |
| Catalase | + |
| OF | F |
| Pigment of colony | NP (note 1) |
| Production of gas from lactose | +(slow) |
| Production of indole | − |
| Methyl red test | + |
| VP test | + |
| Utilization of citric acid (Simmons) | + |
| Production of hydrogen sulfide | − |
| Decomposition of urea | − |
| Phenylalanine deaminase | − |
| Lysine decarboxylase | +(slow) |
| Arginine dihydrolase | − |
| Ornithine decarboxylase | + |
| Liquefaction of gelatine | − |
| Utilization of malonic acid | + |
| Production of acid from glucose | + |
| Production of gas from glucose | − |
| The formation of acids | |
| Cellobiose | + |
| Glycerin | + |
| Maltose | + |
| D-mannose | + |
| L-rhamnose | − |
| Salicin | + |
| Trehalose | + |
| D-xylulose | + |
| Hydrolysis of esculin | + |
| Nitrate reduction | + |
| Decomposition of DNA | − |
| Lipase | − |
| ONPG | + |

-continued

| (Test Items) | (Test results) |
|---|---|
| Intracellular CG content of DNA (mol %) | 54 |
| Type of quinone | Q-8 |

(Note 1) No characteristic colony pigment observed (6) Identification of GSJ/MITA24B/ASHO-RO/2 Mycological Properties The mycological properties of GSJ/MITA24B/ASHO-RO/2 strain and the identified strain were as follows. This strain was the closest to the genus Aeromonas in that it is a motile facultative anaerobic Gram-negative bacillus, and in terms of the CG content of intracellular DNA and the type of quinone. Thus this novel microorganism was named the genus Aeromonas bacterium GSJ/MITA24B/ASHO-RO/2. However, this bacterium could not be deposited with National Institute of Bioscience and Human Technology, Agency of Industrial Science and Technology (1-3, Higashi-1-chome, Tsukuba-shi, Ibaraki-ken 305-0046, Japan), because of its weak activity.

Mycological properties of the strain GSJ/MITA24B/ASHO-RO/2:

| (Test Items) | (Test results) |
|---|---|
| Morphological characters | rod |
| Gram stain | − |
| Spores | − |
| Motility | + |
| Flagella | polar monotrichate |
| Behavior toward oxygen | facultative anaerobic |
| Oxidase | − |
| Catalase | − |
| OF | F |
| Pigment of colony | NP (note 1) |
| Intracellular CG content of DNA (mol %) | 56 |
| Type of quinone | Q-8, MK-8, DMK-8 |

(Note 1) No characteristic colony pigment observed

Identification and mycological properties of the strain GSJ/MITA24C/ASHO-RO/3:

The mycological properties of the strain were as follows. This strain belonged to *Shewanella putrefaciens*. Shewanella is a Gram-negative bacillus having polar flagella and methylmenaquinone (MMK) as type of quinone, and is mainly isolated from aquatic organisms and marine organisms. Moreover, *Shewanella putrefaciens* is a bacterium that was transferred from the genus Alteromonas by MacDonell and Colwell (System. Appl. Microbiol., 6, 171, 1985).

This novel microorganism was named *Shewanella putrefaciens* GSJ/MITA24C/ASHO-RO/3 and deposited with National Institute of Bioscience and Human Technology, Agency of Industrial Science and Technology (1-3, Higashi 1chome, Tsukuba-shi, Ibaraki-ken 305-0046), Japan), as GSJ/MITA24C/ASHO-RO/3. The accession number assigned was FERM P-17220. This deposition was thereafter transferred to an international deposition under the terms of the Budapest Treaty on Dec. 17, 1999, and the accession number FERM BP-6975 was assigned.

Mycological properties of the strain GSJ/MITA24C/ASHO-RO/3:

| (Test Items) | (Test Results) |
|---|---|
| Morphological character | rod |
| Gram stain | − |
| Spores | − |
| Motility | + |
| Flagella | polar monotrichate |
| Behavior toward oxygen | aerobic |
| Oxidase | + |
| Catalase | + |
| OF | O |
| Pigment of colony | brown |
| Requirement for Na+ | + |
| Requirement for salts | |
| Growth on 0% NaCl medium | + |
| Growth on 1% NaCl medium | + |
| Growth on seawater medium | + |
| Decomposition of DNA | + |
| Arginine dihydrolase | − |
| Ornithine decarboxylase | + |
| Lysine decarboxydase | − |
| Production of hydrogen sulfide | + |
| Hemolysis (sheep blood) | + |
| Growth in the presence of 6% NaCl | + |
| Growth at 4° C. | + |
| Growth at 37° C. | + |
| Growth at 42° C. | − |
| Growth on SA agar medium | − |
| Formation of acids | |
| D-ribose | − |
| Maltose | + |
| L-arabinose | + |
| Assimilation | |
| Isoleucine | − |
| Succinate | + |
| Glycerin | − |
| Glucose | + |
| Glucosamine | − |
| Intracellular CG content of DNA (mol %) | 48 |
| Type of quinone | Q-8, Q-7, MMK-7, MK-7 |

Example 2 i. Sampling and Screening of Microbial Symbiont (1) Filtrate (liquid A) is prepared by adding manganese sulfate to a five-fold dilution of artificial seawater (Kester) at a manganese (II) concentration of about 2 to 3 ppm, and filtering the solution through a sterilized filter with a pore size of 0.2 μm.

(2) Green, dark green, brown or black microbial mat is sampled into sterilized sacs or vial. The microbial mat, about 10 percent of the total liquid volume, is put into a sterilized test tube (with a cap) containing the liquid A and is well mixed in a test tube mixer. The liquid is then immediately divided and put into two sterilized test tubes (with a cap, 10 ml each). The microbial mat, to which a fluorescent agent DAPI is added, is observed under the fluorescent microscopy to ascertain the presence of cyanobacteria and bacteria.

(3) One of the test tubes is autoclaved at 121° C. and 2 atmospheric pressure for 15 minutes. It is referred to as a sterilized sample suspension. The other test tube that is not treated is referred to as an untreated (raw) sample suspension.

(4) Three sterilized test tubes (with a cap, 50 ml each), each containing 25 ml of liquid A, are provided. The test tube 1 to which none is added, the test tube 2 to which 2 ml of the sterilized sample suspension is added, and the test tube 3 to which 2 ml of the untreated (raw) sample suspension is added, are prepared.

(5) These three test tubes are well agitated, then subjected to stationary culture under natural light, at 37° C. for four days.

(6) Each of these is filtered through a filter with a pore size of 0.2 μm (no sterilization for filter is required), and is aliquoted into test tubes (about 0.5 ml each).

(7) 0.5 ml of a formaldoxime solution and 0.5 ml of a buffer (pH 10) are added to the test tubes described in (6), respectively, then mixed and left for about 10 minutes.

(8) Reaction liquid from the test tube 1 turns into dark red. If the reaction liquid from the test tube 3 turns into color, significantly weaker than that shown by the one from the test tube 2, the liquid is determined to have a target activity (positive) and is employed. However, if there is almost no difference in color between said test tubes 2 and 3, the liquid is determined to have almost no activity (negative) and is not employed.

(9) The cultures obtained by this screening are effective to remove manganese.

ii. Culturing Microbial Symbiont

Culture of microbial symbiont according to the present invention required no artificial addition of organic matters. One ml of the microbial symbiont, which was screened by the above described screening method, was taken, then added to 9 ml of water to prepare a microbial symbiont sample in a total volume of 10 ml. 0.2 ml of this sample was added to 100 ml of an aqueous solution of artificial seawater (Kester) containing 60 ppm manganese or to 100 ml of sterilized sample water, which has been exposed to the microbial symbiont at the sampling area, and subjected to stationary culture at 37° C. under irradiation of natural light or artificial light.

iii. Treatment of Water Containing Manganese by Microbial Symbiont

A hot-spring water containing manganese at a concentration of 2.4 ppm was filtered through a sterilized filter for sterilization. The sterilized water was then treated as described below, divided into A, B, and C, kept at 37° C., and left under natural light for 3 days.

A: None was added to the sterilized water.

B: B was prepared as follows. A sample with a volume ratio of microbial symbiont grown in (1) to hot-spring water of 1:9 was autoclaved at 121° C. at 2 atmospheric pressure. This sterilized sample, 0.2% (by volume) relative to the sterilized water, was then added to the sterilized water.

C: C was prepared as follows. A sample was prepared to have a volume ratio of microbial symbiont grown in (1) to hot-spring water of 1:9, and this raw sample, 0.2% (by volume) relative to the sterilized water, was then added to the sterilized water.

In addition, Samples A, B, and C are uniformly agitated and left to stand, respectively.

Figure 2:
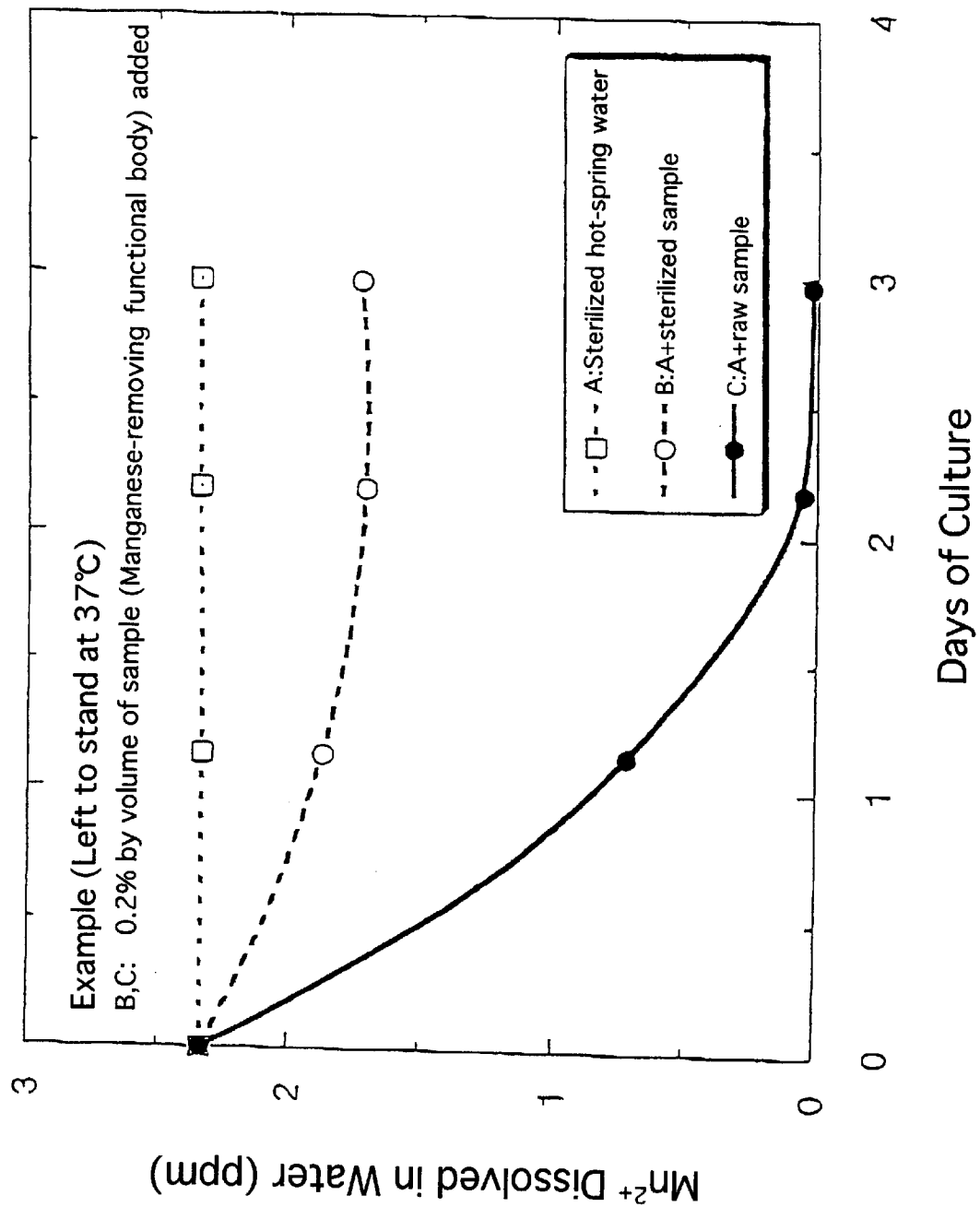
FIG. 2 shows the microbial effect of the removal of manganese in water according to the present invention.

The results are shown in FIG. 2.

The sample A showed no change for three days.

The sample B showed changes in two days. The concentration of manganese ions reduced to 1.8 ppm.

The sample C showed significant changes in two days. On day 3, the concentration of manganese ions dropped to almost zero.

Example 3

Classification and Observation of Microalgae

Unstained microbial colony containing manganese dioxide that was being precipitated was put on a slide glass to observe their internal structure under the phase-contrast microscopy or the bright-field microscopy. The organisms are distinguished between prokariotes with no nucleus in their cells, particularly bacteria and blue-green algae, and eukaryotes with nucleus. Further, self-fluorescence of the chlorophyll emitting an orange fluorescence upon irradiation of ultraviolet light to the unstained sample was observed under the epi-fluorescent microscopy so as to distinguish between algae, such as blue-green algae, green algae, and diatoms, and the other microorganisms. Furthermore, cells to which a fluorescent reagent, DAPI, is added and irradiated with ultraviolet light were observed to detect the distribution of nucleic acids of blue-green algae emitting orange fluorescence as well as the distribution of nucleic acids of bacteria emitting a blue to white fluorescence. According to these results, classification of algae such as blue-green algae, green algae, or diatoms, was carried out referring to a general encyclopedia of microbiology.

Among the algae contained in the microbial symbiont according to the present invention, the existence of blue-green algae such as Oscillatoria, diatoms such as Navicula, and green algae such as Ulothrix was confirmed by observation under the microscopies.

Example 4

Treatment of Water Containing Manganese by Manganese Oxidizing Bacterium

One or more strains of manganese oxidizing bacterium were inoculatd into to artificial seawater to which organic nutrients, such as peptone or yeast extract, are added, or into a five-fold dilution of artificial seawater. This culture system and an uninoculated control system were subjected to shaking culture at 37° C. or 20° C. An aliquot of the liquid was removed to measure the absorbance at 660 nm (optical density, OD 660), cell mass, and dissolved manganese concentration ($Mn^{2+}$).

FIG. 1 shows the results of culture at 20° C. between the system inoculated with one platinum loopful of one or more manganese oxidizing bacteria into 20 ml of 100% artificial seawater (pH 7.5) supplemented with 60 ppm manganese (in initial concentration) and with organic nutrients, and the uninoculated (germ-free) system in the same solution. As can be seen in this figure, manganese dioxide was precipitated even in a liquid with high concentration of salts and a high concentration of manganese ions could be removed from a solution in which manganese dioxide is not precipitated chemically.

Moreover, the recovered manganese can be recycled as a raw material for manufacture of products such as dry batteries and glazing agents.

The microorganisms and microbial symbiont according to the present invention have not been artificially isolated and cultured so far. The method for removing heavy metals, particularly manganese, by the use of this microbial symbiont does not need to elevate alkalinity of various water containing manganese to pH10 or more. Therefore, the method can be applied to waste-water treatment and manganese can be removed at low cost.

Further, the treatment method allows manganese dioxide to be recycled from waste matters containing manganese, such as used dry batteries and used iron materials.

Moreover, manganese dioxide precipitate obtained by this method is in high grade so that it can be effectively used as a material for manufacturing products such as dry batteries, iron, glazes and glasses.

This specification includes part or all of the contents as disclosed in the specification and/or drawings of Japanese Patent Application No. 10-377190 and No. 11-112735, which are priority documents of the present application.

What is claimed is:

1. A biologically pure culture of algae and manganese oxidizing bacteria, wherein said manganese oxidizing bacteria are selected from the group consisting of Cedecea FERM BP6974 and Shewanella FERM BP6975.

2. The culture of claim 1, wherein the culture is devoid of extraneous organic matter.

3. The culture of claim 1, wherein said algae are selected from the group consisting of blue-green algae, diatoms, and green algae.

4. The culture of claim 1, wherein said algae are selected from the group consisting of Oscillatoria, Navicula, and Ulothrix.

5. The culture of claim 1, wherein the culture is suspended in a sludge of a manganese mineral deposit.

6. The culture of claim 5, wherein the culture is diluted with artificial seawater.

7. The culture of claim 6, wherein a 0.5- to 20 fold dilution of artificial seawater is used.

* * * * *